United States Patent [19]

Wootton et al.

[11] Patent Number: 5,231,029
[45] Date of Patent: Jul. 27, 1993

[54] APPARATUS FOR THE IN SITU HYBRIDIZATION OF SLIDE-MOUNTED CELL SAMPLES

[75] Inventors: Richard Wootton, London; Alastair G. McLeod, Coventry; Raymond Read, Stanmore, all of United Kingdom

[73] Assignee: Royal Postgraduate Medical School, London, England

[21] Appl. No.: 793,341

[22] PCT Filed: Aug. 21, 1990

[86] PCT No.: PCT/GB90/01310
§ 371 Date: Jan. 14, 1992
§ 102(e) Date: Jan. 14, 1992

[87] PCT Pub. No.: WO91/02962
PCT Pub. Date: Mar. 7, 1991

[30] Foreign Application Priority Data
Aug. 23, 1989 [GB] United Kingdom ............... 8919145

[51] Int. Cl.[5] ............... C12Q 1/68; G01N 1/30
[52] U.S. Cl. .................... 435/289; 422/67; 435/316; 435/809; 436/46; 436/47; 436/49; 436/50; 436/174
[58] Field of Search ............... 435/289, 290, 809, 316; 422/65, 66, 63, 67; 436/46, 47, 49, 50, 174; 118/324, 300; 239/302; 137/205, 206

[56] References Cited

U.S. PATENT DOCUMENTS

| | | | |
|---|---|---|---|
| 3,650,437 | 3/1972 | Binnings et al. | 436/800 X |
| 3,875,899 | 4/1975 | Clements | 118/324 X |
| 4,004,550 | 1/1977 | White et al. | 118/314 X |
| 4,013,038 | 3/1977 | Rogers et al. | 118/5 |
| 4,043,292 | 8/1977 | Rogers et al. | 118/59 X |
| 4,543,236 | 9/1985 | Von Gise | 422/50 |
| 5,009,185 | 4/1991 | Stokes et al. | 118/314 X |

FOREIGN PATENT DOCUMENTS
1455295A1 6/1986 U.S.S.R. .

*Primary Examiner*—James C. Housel
*Assistant Examiner*—Long V. Le
*Attorney, Agent, or Firm*—Nixon & Vanderhye

[57] ABSTRACT

Apparatus for the in situ hybridization of slide-mounted cell samples contains modules for the three processes required: (a) reagent metering and spreading on a slide (1) which is effected by drawing a quantity of reagent (56-59) into a reservoir (31) and then spraying it on the slide (1) using air pressure. The rate of flow through the spray is ascertained by measurement and the dosage determined by timing the spraying; (b) slide washing; and (c) slide incubation. The slide washing and incubation are performed in the same dual-purpose housing (16). A high humidity level is maintained in the housing during incubation so that the samples do not need to be covered to prevent them drying out. A plurality of slides (1) are mounted in a carrier (11) to be washed and incubated at the same time.

19 Claims, 1 Drawing Sheet

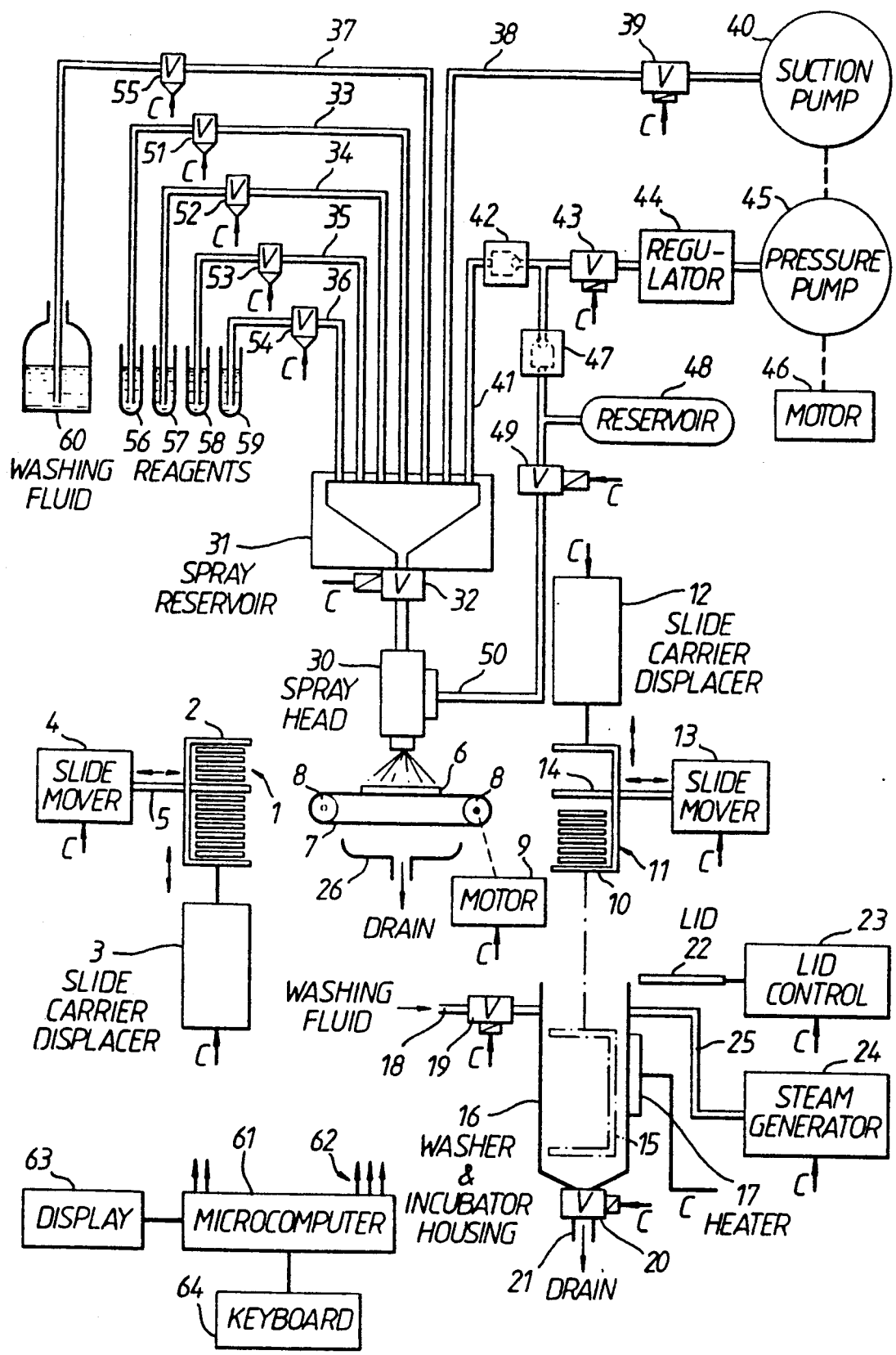

APPARATUS FOR THE IN SITU HYBRIDIZATION OF SLIDE-MOUNTED CELL SAMPLES

This invention relates to in situ hybridization and in particular to apparatus for effecting hybridization of cell samples carried on slides.

A powerful technique which has been developed for detecting particular sequences of nucleic amino-acids in a segment of DNA is known as in situ hybridization. This technique uses a chemically or radioactively labelled "probe" to hybridize the DNA of tissue samples in situ, the samples which become labelled can then be detected by the physical or chemical properties of their chemical label or their radioactivity. Because of the risk to the health of the operator through the use of radioactive materials, chemically labelled probes may be preferred.

The process of in situ hybridization requires the treatment of samples on a microscope slide, for example, with measured small quantities, say 50 $\mu$liters, of reagents such as enzymes. The reagents are applied by pipette or other hand-held dispenser to the slide and then spread evenly over the surface. These pre-hybridization reagents are then washed off in, say, phosphate buffered solution (PBS) and a hybridization "cocktail" of further reagents applied in the same way as the first reagents. The samples are then covered by a glass cover-slip or a film of inert plastics material to prevent them drying out during incubation which may extend for a period between say 30 minutes and 16 hours or even more. After that the cover-slip or film may be removed, the slide washed in, say, phosphate buffered solution (PBS), further reagents applied and incubation carried out for a second period. There are many different "recipes" for in situ hybridization, some involving several treatments with reagents and several incubations. It is evident that the process must be performed carefully by skilled personnel and that it is very time-consuming. It is therefore desirable to reduce the labour content of the process without compromising the care and accuracy of the treatment of the samples.

It is an object of the present invention to provide a machine which is capable of performing in situ hybridization on slide-mounted tissue samples.

According to the present invention there is provided apparatus for the in situ hybridization of slide-mounted cells samples in which slides bearing samples are brought successively to a station to be sprayed with one or more fluid reagents by a spray means and thereafter are subjected to incubation to further the process, the spray means including a reservoir into which a fluid reagent can be fed and a spray head to which the fluid reagent can be passed from the reservoir for spraying on a sample on a slide, wherein the apparatus includes at least one container for containing a fluid reagent, pipe means leading from the or each container to the reservoir, valve means selectively effective to block and to permit flow along the pipe means, and means for selectively establishing an air pressure difference between the or each container and the reservoir, the arrangement being such that the air pressure difference can cause fluid to flow from a particular container into the reservoir when the corresponding valve means is such as to permit flow along the pipe means, the valve means being operated to permit a predetermined volume of a fluid reagent to be fed to the reservoir.

The feeding of the fluid into the reservoir and the passing of the fluid from the reservoir to the spray head may be effected at least partly by air pressure. The air pressure may be provided by a higher than atmospheric pressure applied to the fluid to cause it to flow to a region held at atmospheric pressure or it may use atmospheric pressure to cause the fluid to flow to a region where a pressure below atmospheric pressure is maintained.

The apparatus may include a container for containing fluid subject to atmospheric pressure, with the pipe means leading from the container to the reservoir, and the valve means selectively effective to block and to permit flow along the pipe means, and a suction pump selectively connectible to draw air from the reservoir. The apparatus may include a plurality of such containers respectively for containing different fluids and having associated therewith respective valve means selectively effective to block and to permit flow of the fluid from the containers to the reservoir. The rate of flow of the fluid along the pipe means may be measured under predetermined conditions and the result used to determine the time for which the valve means is opened to allow a required quantity of the fluid to be fed into the reservoir.

The spray head may be arranged to receive air under pressure at the same time as the fluid is fed to it and the air flow used to produce a fine even spray of the fluid.

The slides bearing samples may be mounted in parallel planes in a carrier to facilitate handling. The carrier may be indexed past an entry port to the spary station where a conveyor brings the slides one at a time beneath the spray head.

The apparatus may include a heatable incubator capable of receiving a carrier containing slides. The incubator housing may be closable and means may be provided for injecting steam into the incubator to establish therein the humidity level just below 100 percent so as to prevent the samples from drying out during incubation. The incubator housing may also be arranged to contain a washing fluid to enable slides in a carrier to be washed, possibly with agitation of the carrier.

The apparatus may include computer means programmed to control the operation of the spray means and the incubation to effect part or all of an in situ hybridization process. The program may be adjustable under the control of an operator to provide several choices of hybridization process.

BRIEF DESCRIPTION OF THE DRAWING

An example of an apparatus for automatically performing in situ hybridization slide-mounted cell samples is shown in diagrammatic form in the single FIGURE of the accompanying drawing to which reference will now be made.

DESCRIPTION OF THE PREFERRED EMBODIMENT

A plurality of slides 1 bearing cell samples for in situ hybridization is mounted in a carrier 2, which is movable in the up and down directions by a displacer 3. The movement of the carrier 3 is arranged to bring the slides successively level with an arm 5 which is movable from left to right under the control of a slide mover 4 to take a slide from the carrier 2 or to return a slide to it. A slide 6 has been moved by the slide mover 4 on to a conveyer belt 7 which runs round rollers 8 which are rotated by a motor 9.

A second slide carrier 10, in which are mounted further slides 11, is movable under the control of a second slide carrier displacer 12. An arm 14 controlled by a second slide mover 13 can receive slides from the belt 7 for transfer to the carrier 10 or can transfer slides from the carrier 10 to the belt 7.

Whereas the slide carrier displacer 3 is only capable of moving the carrier 2 in steps to bring each slide in turn into line with the arm 5, the slide carrier displacer 12 can perform the same operation and can also move the carrier 10 and the slides mounted in it to a position 15 in which it is inside a washer and incubator housing 16.

The washer and incubator is provided with a heater 17 which is arranged to maintain the interior of the housing 16 at a thermostatically controlled temperature. Instead of or in addition to the heater 17 a refrigerator means (not shown) may be provided to enable the interior of the housing to be maintained at a temperature below ambient where such is required for the treatment of the slides. For washing the slides in the carrier 15, a washing fluid such as, for example, PBS, can be fed through a pipe 18 and a valve 19 into the housing 16. The washing fluid flows from a reservoir (not shown) of similar design but of larger capacity than the reservoir 31 for the reagents described below, into which different washing agents can be fed in the same way as the reagents are fed into the reservoir 31. In order to improve the efficiency of the washing, the carrier 15 may be agitated by the displacer 12. Alternatively, the washing fluid may be stirred by a rotor or circulated by means of a pump. When the slides have been washed, the used washing fluid may be allowed to drain out by opening a valve 20 to allow the fluid to pass down the pipe 21 into the drain. When it is used as an incubator, the housing 16 is closed by a lid 22, which is moved into position by a lid control unit 23. In order to prevent the samples on the slides from drying out during incubation, steam from a generator 24 is fed through a pipe 25 into the housing 16 to raise the humidity inside it to be close to 100 percent at the incubation temperature. It is important that the amount of water in the atmosphere in the housing 16 should not be too high as this would cause the undesirable condensation of water on the slides.

It may be required to maintain an air pressure above atmospheric within the housing 16 during incubation to reduce evaporation from the samples. The housing 16 may be constructed to allow that and a suitable pump may be provided for the purpose.

Another modification which could be made to the housing 16 or in the same region of the apparatus is to provide some means for directing a current of cooling air, preferably of suitable humidity, to cool the slides after incubation.

For applying reagents to the slide 6, a spray head 30 is provided which receives a reagent from a reservoir 31 under the control of a valve 32. The reservoir 31 is of a closed funnel shape and has input pipes 33, 34, 35 and 36, through which different reagents can be fed into the reservoir and a pipe 37 through which a washing fluid can be fed into it. The reagents and washing fluid are drawn into the reservoir 31 by suction applied via a pipe 38 which is connected through a valve 39 to a suction pump 40. The pipe 37 is preferably so placed that the washing fluid flushes round the reservoir 31 as it enters so as to remove residual traces of reagent. In order to expel the reagent in the reservoir 31 towards the spray head 30, air pressure is applied to the reservoir via a pipe 41. The pipe 41 is connected through a non-return valve 42, a valve 43 and a pressure regulator 44 to a pressure pump 45. The suction pump 40 and the pressure pump 45 are both driven by a motor 46. In addition to being connected to a one-way valve 42, the output of the valve 43 is also connected through a second one-way valve 47 to a reservoir 48 and from that through a valve 49 to a pipe 50 connected to the spray head 30. The pipes 33, 34, 35 and 36 are provided with valves 51, 52, 53 and 54 to control the flow of reagents from tubes 56, 57, 58 and 59 respectively in which they are stored. A valve 55 controls the flow of washing fluid from a storage bottle 60 along the pipe 37.

A microcomputer 61 is provided with a plurality of control outputs 62 which are respectively connected to the control inputs, labelled C, of the slide carrier displacers 3 and 12, the slide movers 4 and 13, the motor 9, the heater 17, the lid control unit 23, the steam generator unit 24 and the valves 19, 20, 32, 39, 43, 47, 49, 51, 52, 53, 54 and 55. The microcomputer 61 contains a program for operating the components of the apparatus in the correct order and for the appropriate periods of time or to the appropriate amount to effect a required in situ hybridization process. The parameters of this process are adjustable by an operator and the program is arranged to display a menu of choices on a display unit 63, so that the operator can enter by means of keyboard 64 the choices which he wishes to make.

An example of the apparatus shown in the FIGURE is shown in diagrammatic form because the shapes and dispositions of the various components can be changed considerably without affecting the fundamental operation. For example, the slide carriers 2 and 10 need not be of the simple linear form shown but could be toroidal form similar to that used for handling photographic slides for projection. In fact, the techniques used for handling photographic slides could be used for handling the slides in this apparatus. Only a single slide carrier need be provided and the carrier 2 and the mechanisms for moving it and for selecting slides from it could be omitted. The conveyor belt 7 could be replaced by a disc rotating about a vertical axis having recesses in its periphery for receiving slides and being arranged to be rotated in steps by a suitable mechanism to bring the slides successively into position beneath the spray head 30. Similarly, changes could be made to the configuration of the washer and incubator; if desired, these two functions could be performed by separate parts which would have the advantage of permitting the washing of some slides while other slides are being incubated.

An in situ hybridization process includes three fundamental tasks, namely:
1. reagent metering and spreading on the slide;
2. slide washing;
3. slide incubation.

The performance of these three operations by the apparatus shown will now be described.

The reagents to be spread on the slides are stored in the tubes 56 to 59. In practice, more than four tubes may be provided and in one example fourteen such tubes are provided and there could be even more tubes than that if required. In order to apply the reagent in the tube 56 to the slide 6, some of the reagent is drawn into the spray reservoir 31 by opening the valve 39 so that the pressure in the reservoir 31 is reduced and then the valve 51 is opened allowing the reagent to be sucked along the pipe 33 into the reservoir 31. At this time all other valves controlling pipes connected to the reservoir 31 are closed. When a sufficient quantity of the reagent has been transferred to the reservoir 31, the valves 39 and 51 are closed. Air pressure above atmospheric pressure is now applied to the reservoir 31 by opening the valve 43 allowing pressure of the level set by the regulator 44 to be established in the reservoir 31. The same air pressure is also established in the reservoir 48 for use in dispersing the reagent as a fine spray by the spray head 30 using air flow along the pipe 50 when the valve 49 is opened. The air flow also helps to cut off cleanly the flow of reagent. Prior to the use of the apparatus for spraying the reagent on to the slides, the rate of flow of reagent through the valve 32 under the influence of the regulated air pressure established in the reservoir 31 is ascertained by measurement and on the basis of this measurement the duration of the opening of the valve 32 needed to produce the required dosage of reagent is calculated. When the valve 32 is opened, the reagent flows through it into the spray head 30 and the reagent is distributed as a fine spray over the slide 6 whilst the valve 32 is kept open for the required period. If more than one reagent is to be applied to a slide, then the required reagents can be drawn into the reservoir 31 by separate opening of the valves 51, 52, 53 and 54, as required. The flow characteristics of the valves 51 to 54 may be measured in the same way as described above for the valve 32 so that the required proportions of the different reagents are drawn into the reservoir 31. Preferably, the measurements are performed on the apparatus itself because factors such as the lengths of the pipes and the bends in them can influence the delivery.

In one example of the apparatus, the valves 39, 43 and 49 which control air flow are solenoid valves of conventional construction, for example, REEDEX types V22 IP5-2PNS and V32 IP5-2BNS. The former type is used for the valve 49 and the latter type for the valves 39 and 43. The suction pump 40 is arranged to provide a pressure of −10.8 psig relative to atmospheric pressure, and the regulator 44 is arranged to control the positive pressure to a value of 25 psig above atmospheric pressure. The valves 51 to 55 are solenoid pinch valves of the type ALPHA NC P/N 161 P011 with the pipes 33 to 37 being formed of flexible plastics tubing. The valve 32 is a LEE 3/2 solenoid valve LFAA 1201618 H. The spray head 30 is of the type LEE INSTAC liquid dispenser TCDA 6201110K. Of course, other suitable types of valve and spray head may be used.

It has been found convenient for the tubes 56 to 59 and the bottle 60 to be carried on a detachable rack with the pipes 33 to 37 held in fixed positions.

The washing of slides is effected by placing a carrier in which the slides are mounted in the housing 16, filling the housing with a washing fluid such as, for example, PBS, which is maintained at a required temperature by the heater 17. The carrier with the slides in it may be agitated by the displacer 12 to improve the effectiveness of the washing. Several different washing fluids may be used and separate valve controlled inputs for the different fluids may be provided.

When slides are to be incubated, they are placed in the housing 16 on a carrier and the lid 22 of the housing closed. Steam from the generator 24 is fed into the housing 16 as the temperature in it is raised so as to maintain the humidity of the atmosphere at about 95 percent, thereby reducing to a low value the moisture loss due to evaporation from the tissue samples on the slides. Initially, to denature the DNA content of the cells of the samples, they are heated to 100° C. and then rapidly cooled to room temperature. This rapid cooling could be achieved by means of water circulating in a jacket in the housing 16 or air blown around carrier 15 whilst in housing 16.

A typical slide-mounted sample may require a dosage of between 10 and 50 µliters of the reagent to be applied in order to achieve efficient penetration of the cell membranes of the sample. It is necessary to maintain the stipulated volumes of reagents because if insufficient reagent is applied then the hybridization will be incomplete or possibly ineffective. On the other hand, the reagents required for hybridization are expensive and if excessive quantities are used this will be economically wasteful. Generally, the reagents take the form of small volumes of active material dissolved in a buffer solution such as PBS which has a density and viscosity similar to that of water. However, the hybridization "cocktail" contains reagents which are diluted in a 10 percent solution of dextran sulphate which has a higher density and viscosity than of those of water. The flow characteristics of the valves are therefore measured for both buffer solutions and dextran sulphate. In each case, the quantities passed by the valves for periods of up to 2 seconds in quarter second steps are measured and corresponding calibration data stored in the microcomputer. It was found that for volumes of reagent less than 6 µliters, a simple linear factor was inadequate, but this is not significant because for most hybridization procedures the minimum quantity of reagent used is 10 µliters.

As the apparatus is required to spray different reagents at different times, it is necessary to be able to wash out residual traces of one reagent from both the reservoir 31 and the spray head 30 before drawing the next reagent or group of reagents into the reservoir 31. This washing out is usually done with PBS, although other washing fluids may be used. Tests have shown that if the reservoir is flushed more than once with PBS after one reagent, then the contamination of the following reagent is insignificant.

Various modifications can be made to the apparatus described apart from the alteration of the number of storage tubes for reagents and the associated valves and pipes and the addition of alternative washing fluids and the containers and feed pipes for them. For example, instead of using air pressure to transfer amounts of reagent or washing fluid to the reservoir gravity feed may be used. The air pressure feed of reagent from the reservoir to the spray head may be replaced by gravity feed although air dispersion of the reagent to form a spray could still be used. As another alternative to gravity feed a pump, such as a peristaltic pump, may be used. A storage place may be provided for carriers containing slides so that they can be prepared and placed in the apparatus for processing in their turn. As mentioned above, other configurations of slide carrier than the one shown may be used with suitable modification to the displacers. The apparatus may be of modular construction, with separate modules for reagent spraying, slide transport, slide washing and slide incubation connectible together in different arrangements. Refrigeration means may be provided to keep cool all or part of the apparatus if required.

We claim:

1. Apparatus for the in situ hybridization of slide-mounted cell samples in which slides bearing samples are brought successively to a station to be sprayed with one or more fluid reagents and thereafter are subjected to incubation, the apparatus comprising a spray means including a reservoir into which a fluid reagent is fed and a spray head to which the fluid reagent is passed from the reservoir for spraying on a sample on a slide, the apparatus further comprising at least one container for containing the fluid reagent, pipe means leading from the at least one container to the reservoir, valve means selectively effective to block and to permit flow along the pipe means, and means for selectively establishing an air pressure difference between the at least one container and the reservoir, the apparatus being such that the air pressure difference causes fluid to flow from the at least one container into the reservoir when the valve means is such as to permit flow along the pipe means, the valve means being operated to permit a predetermined volume of the fluid reagent to be fed to the reservoir.

2. Apparatus according to claim 1 including a plurality of containers for containing a plurality of fluid reagents respectively connected by different pipe means to the reservoir and having respectively associated therewith valve means selectively effective to block and to permit flow along the pipe means, so that by operation of the valve means different fluid reagents may be permitted to flow into the reservoir.

3. Apparatus according to claim 2 wherein the valve means is opened for a particular time period to allow a particular amount of the fluid reagent to be fed into the reservoir.

4. Apparatus according to claim 1, wherein the passing of a fluid reagent from the reservoir to the spray head is caused at least partly by air pressure and air is also fed to the spray head so as to produce a fine, even spray of fluid.

5. Apparatus according to claim 4 wherein the reservoir includes outlet valve means and an air pressure is generated above atmospheric pressure in the reservoir for expelling fluid reagent stored in the reservoir when the outlet valve means is open.

6. Apparatus according to claim 5 wherein the outlet valve means is opened for a time period such as to allow a predetermined volume of the fluid reagent to be sprayed on a slide.

7. Apparatus according to claim 1, wherein slides bearing samples are held in parallel planes in a first carrier which is moved in steps past a slide mover which serves to convey one slide at a time to the station for spraying.

8. Apparatus according to claim 7 including a second carrier into which the slides can be transferred from the station.

9. Apparatus according to claim 8 including an incubator housing capable of being maintained at a required temperature for receiving the second carrier containing slides, wherein the incubator housing can be closed with the second carrier inside it and includes means for providing steam in the incubator housing to establish therein a humidity level of about 100 percent so as to prevent the samples from drying out during incubation.

10. Apparatus according to claim 9 wherein the incubator housing can contain a washing fluid to enable slides in the second carrier to be washed.

11. Apparatus according to claim 9 including a receptacle for a fluid for washing the slides separate from the incubator housing.

12. Apparatus according to claim 10 including means for agitating the carrier in the washing fluid contained in the incubator housing.

13. Apparatus according to claim 10 including means for stirring or circulating the washing fluid when the carrier is in the incubator housing.

14. Apparatus according to claim 10 including reservoir means, means for charging the reservoir means with a predetermined amount of a selected one of a plurality of washing fluids and means for transferring the predetermined amount of the selected washing fluid from the reservoir means to the incubator housing for washing the slides in the second carrier.

15. Apparatus according to claim 1 including computer means programmed to control the operation of the spray means and the incubation to effect at least part of an in situ hybridization process.

16. Apparatus according to claim 15 wherein the computer means includes display means and is so programmed as to present a menu of choices for different stages of the process.

17. Apparatus according to claim 11 including means for agitating the carrier in the washing fluid receptacle.

18. Apparatus according to claim 11 including means for stirring or circulating the washing fluid when the carrier is in the washing fluid receptacle.

19. Apparatus according to claim 11 including reservoir means, means for charging the reservoir means with a predetermined amount of a selected one of a plurality of washing fluids and means for transferring the amount of the selected washing fluid from the reservoir means to the receptacle for washing the slides in the second carrier.

* * * * *